US012503411B2

(12) United States Patent
Klavers et al.

(10) Patent No.: US 12,503,411 B2
(45) Date of Patent: Dec. 23, 2025

(54) LOW CO2 EMISSION ETHANE CRACKER

(71) Applicant: KELLOGG BROWN & ROOT LLC, Houston, TX (US)

(72) Inventors: Hendrik Wolterus Klavers, Houston, TX (US); Rian Reyneke, Katy, TX (US); Mark Philip Loring, Kerrville, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 17/880,973

(22) Filed: Aug. 4, 2022

(65) Prior Publication Data

US 2024/0043355 A1 Feb. 8, 2024

(51) Int. Cl.
*C07C 4/04* (2006.01)

(52) U.S. Cl.
CPC .................................... *C07C 4/04* (2013.01)

(58) Field of Classification Search
None
See application file for complete search history.

(56) References Cited

U.S. PATENT DOCUMENTS 4,617,109 A 10/1986 Wells et al.
4,663,493 A * 5/1987 Vora ........................ C07C 5/321 585/314
5,120,892 A * 6/1992 Skraba ..................... C10G 9/00 585/650
11,512,257 B1 * 11/2022 Spicer ................ B01D 53/1475

FOREIGN PATENT DOCUMENTS

RU 2764677 C2 1/2022
WO WO-2021052642 A1 * 3/2021 ............ C10G 9/002

OTHER PUBLICATIONS

Eurasian Patent Organization (EAPO); Eurasian Application No. 202493177/28; Office Action dated Apr. 22, 2025; 3 pages.

* cited by examiner

*Primary Examiner* — In Suk C Bullock
*Assistant Examiner* — Alyssa L Cepluch
(74) *Attorney, Agent, or Firm* — Gary M. Machetta

(57) ABSTRACT

Low carbon dioxide-emitting processes and systems for steam cracking hydrocarbons to produce products such as ethylene are described. The processes and systems involve cracking the feed in a furnace that is configured to burn a hydrogen-rich fuel, which produces less carbon dioxide than methane, which is typically used as fuel for such furnaces. The hydrogen-rich stream can be isolated and recycled from the cracker tail gas.

11 Claims, 3 Drawing Sheets

LOW CO2 EMISSION ETHANE CRACKER

FIELD OF THE INVENTION

This application relates to steam cracking of hydrocarbon feeds, in particular ethane. More specifically, this application relates to steam cracking systems with low $CO_2$ emissions.

INTRODUCTION

Ethylene is an important petrochemical intermediate used to make a variety products. Ethylene can be produced from ethane-rich hydrocarbon feedstocks using a process known as steam cracking. During steam cracking, the hydrocarbon feedstock is mixed with steam (known as dilution steam) and heated to cracking temperatures to crack the hydrocarbons in the feed into smaller molecules, producing ethylene and co-products.

An ethane steam cracking plant uses furnaces to heat the ethane and dilution steam used during the cracking reaction. A portion of the waste heat from the furnaces is used to make steam to provide heat for making dilution steam and for other components of the process, such as refrigeration turbines, etc. When the furnace provides sufficient heat for all of the needed steam, the system is said to be in "steam balance."

When the ethane-rich hydrocarbon feed is cracked it produces a cracked product stream that comprises ethylene, as well as other products, such as methane (CH4), hydrogen (H2), and carbon dioxide (CO2). The cracked product stream can be separated into ethylene product and a tail gas stream comprising methane and other components. A portion of the tail gas stream can be used as fuel for the furnace burners. In other words, the cracking reaction can provide some or all of the fuel needed for the burners. When the cracking reaction produces sufficient fuel (in the form of tail gas) to sustain the operation of the burners, the system is said to be in "fuel balance."

In a typical ethane cracker, the tail gas may comprise about 80-85 mol % H2, with the balance comprising mostly CH4. When the tail gas is burned in the furnaces, a significant amount of CO2 is produced because of the CH4 present in the fuel/tail gas. There is a need to reduce the amount of CO2 produced during ethane cracking.

SUMMARY

Disclosed herein is a process for steam cracking a feed comprising hydrocarbon feedstock and steam, the process comprising: heating the feed in a furnace to produce a cracked gas stream comprising methane (CH4), ethylene, and hydrogen (H2), separating the cracked gas stream into a product stream enriched in ethylene and a tail gas stream that is enriched in CH4 and H2, separating the tail gas stream into a CH4-enriched stream and a H2-enriched stream that is enriched in H2, recycling at least a portion of the H2-enriched stream to the furnace as a fuel stream for furnace burners, mixing the fuel stream with combustion air to form a combustion mixture, and burning the combustion mixture in the furnace burners. According to some embodiments, the hydrocarbon feedstock comprises ethane. According to some embodiments, recycling at least a portion of the H2-enriched stream to the furnace comprises expanding the H2-enriched stream in an expander to produce an expanded H2-enriched stream and recycling the expanded H2-enriched stream to the furnace as the fuel stream.

According to some embodiments, the H2-enriched stream has a pressure of greater than 20 barg and the expanded H2-enriched stream has a pressure of less than 10 barg. According to some embodiments, expanding the H2-enriched stream drops the temperature of the stream, such that the expanded H2-enriched stream is colder than the H2-enriched stream. According to some embodiments, separating the tail gas stream into the hydrocarbon-enriched stream and the H2-enriched stream comprises cooling the tail gas stream using heat exchange against the expanded H2-enriched stream. According to some embodiments, none of the hydrocarbon enriched stream is used as fuel for the furnace burners. According to some embodiments, the fuel stream comprises greater than 90 mol % H2. According to some embodiments, the furnace comprises a radiant section and a convection section. According to some embodiments, the process further comprises preheating the combustion air using heat from flue gas in the convection section before the combustion air is mixed with the fuel stream. According to some embodiments, the combustion air is preheated to at least 350° C. before the combustion air is mixed with the fuel stream. According to some embodiments, the process further comprises heating the feed by heat exchange against the cracked gas stream. According to some embodiments, the process further comprises heating the feed in a feed preheater using heat from flue gas in the convection section. According to some embodiments, the process further comprises heating the feed by heat exchange against the cracked gas stream to at least 350° C. and then heating the feed to at least 650° C. in a feed preheater using flue gas heat in the convection section. According to some embodiments, the furnace fuel demand is satisfied using only the H2-enriched stream as a fuel stream for furnace burners. According to some embodiments, the process further comprises superheating steam in one or more steam superheaters using heat from flue gas in the convection section.

DETAILED DESCRIPTION

Figure 1:
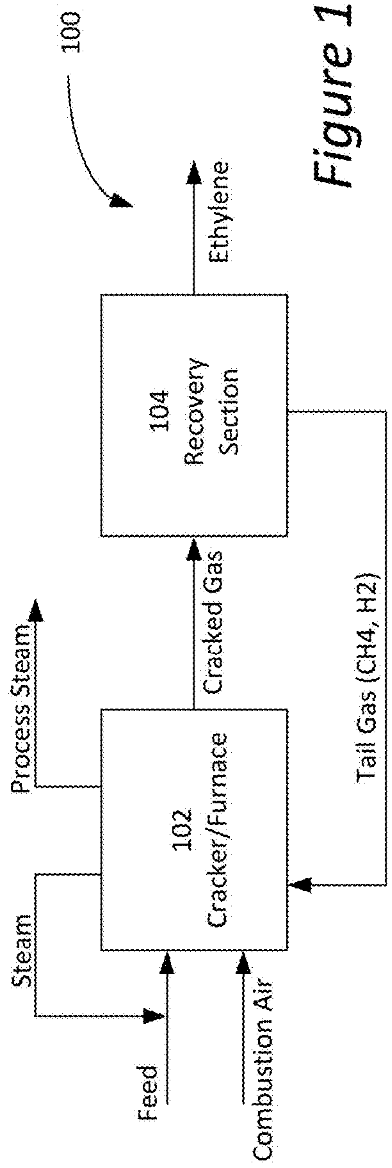
FIG. 1 shows a high-level block diagram of a steam cracking process.

Aspects of this disclosure relate to reducing CO2 emissions from furnace burners used in hydrocarbon steam cracking processes. The disclosure is particularly relevant to ethylene production processes wherein an ethane-rich stream is steam cracked to yield ethylene. FIG. 1 is a high-level schematic of a typical steam cracking process 100. As described above, a feed gas is mixed with steam and cracked in a furnace 102. Heat from the furnace is also used to produce steam. The produced steam may be let down through turbines and then used as diluent steam for the cracking reaction. The steam may also be used as process steam for other aspects of the system, such as refrigeration compressors, etc. The cracker effluent gas (i.e., the cracked gas) from the cracking reaction is provided to a recovery section 104. The recovery section is configured to isolate the ethylene product from the other components of the cracker effluent. In other words, the recovery section yields an ethylene-enriched stream and an ethylene-depleted tail gas stream. The tail gas stream comprises CH4, H2, and small amounts of other components. As described above, some or all of the tail gas stream can be recycled to the furnace and used as fuel for the furnace burners.

Figure 2:
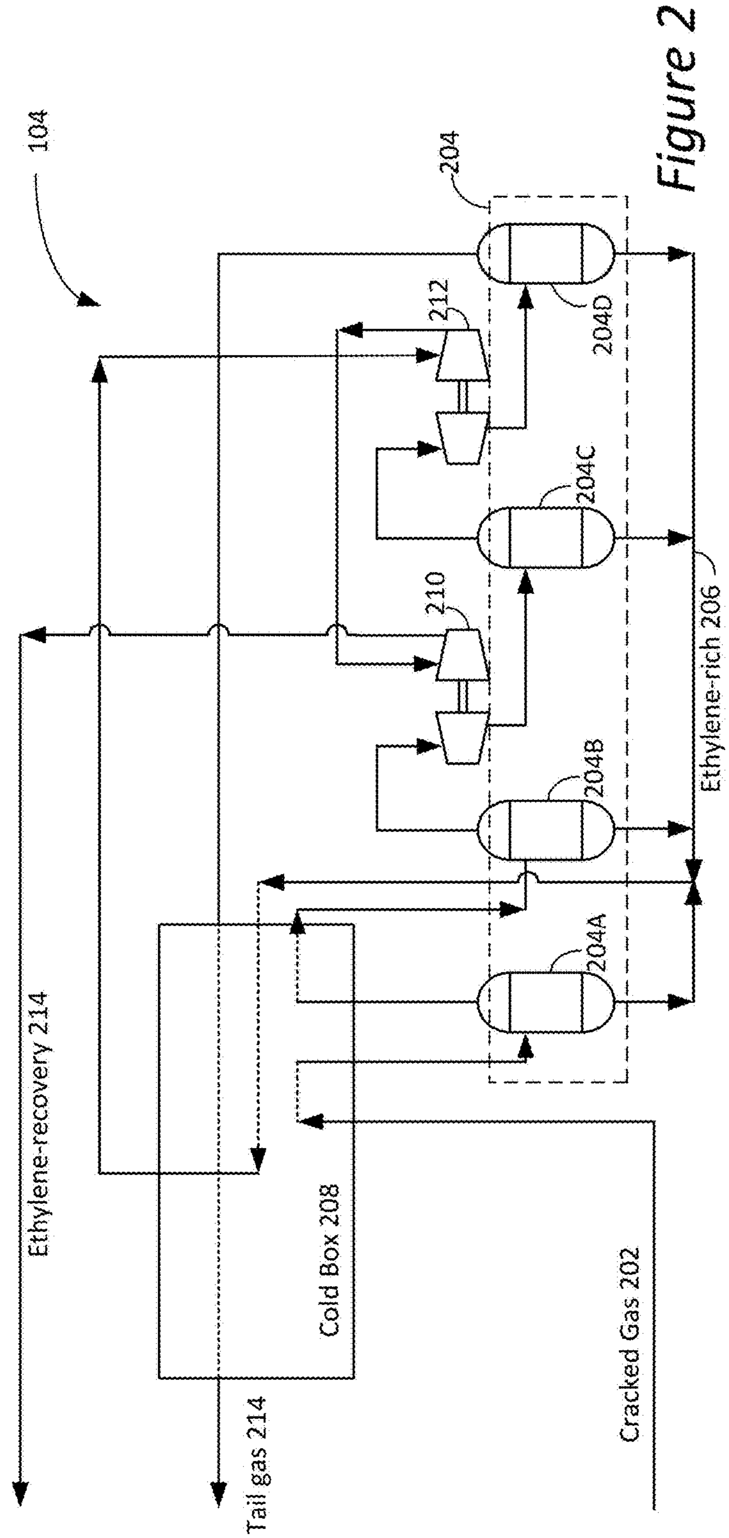
FIG. 2 shows a generalized recovery section process for a steam cracking process.

FIG. 2 illustrates a more detailed schematic of an embodiment of a portion of the recovery section 104 of a typical ethane cracker. Cracked gas comprising CH4, H2, and ethylene (line 202) is progressively cooled and a series of knock-out drums 204 (i.e., drums 204A-204D) are used to knock out ethylene from the effluent stream. Ethylene (and small amounts of methane) knocked out by each of the drums 204A-204D is combined in a combined ethylene-rich stream 206. In illustrated embodiment, the ethylene-rich stream 206 is routed through a cold box 208 (e.g., a plate-fin exchanger), compressed using turbo expander/compressors 210 and 212, and provided from the recovery section as an ethylene recovery stream 214, which may be recycled to the process for recovery. The top streams of each of the knock-out drums is enriched in CH4 and H2 and depleted with respect to ethylene. The CH4 and H2 exit the system as a single, low-pressure, tail gas stream 214. Typically, the tail gas comprises about 80 to about 85 mol % H2 with the balance being mostly CH4.

As described above, the tail gas may be recycled to the furnace as fuel for the burners, Since the tail gas contains a substantial amount of CH4, the burning of that tail gas in the burners generates a substantial amount of CO2. The inventors have found that the amount of CO2 generated by the burners can be reduced by separating the tail gas into a stream that is enriched in H2 (and depleted in CH4) and using the H2-enriched tail gas as fuel for the burners. Specifically, embodiments of the disclosure provide processes for producing a low-pressure H2-enriched tail gas stream as fuel for the burners in an ethane steam cracking furnace.

Figure 3:
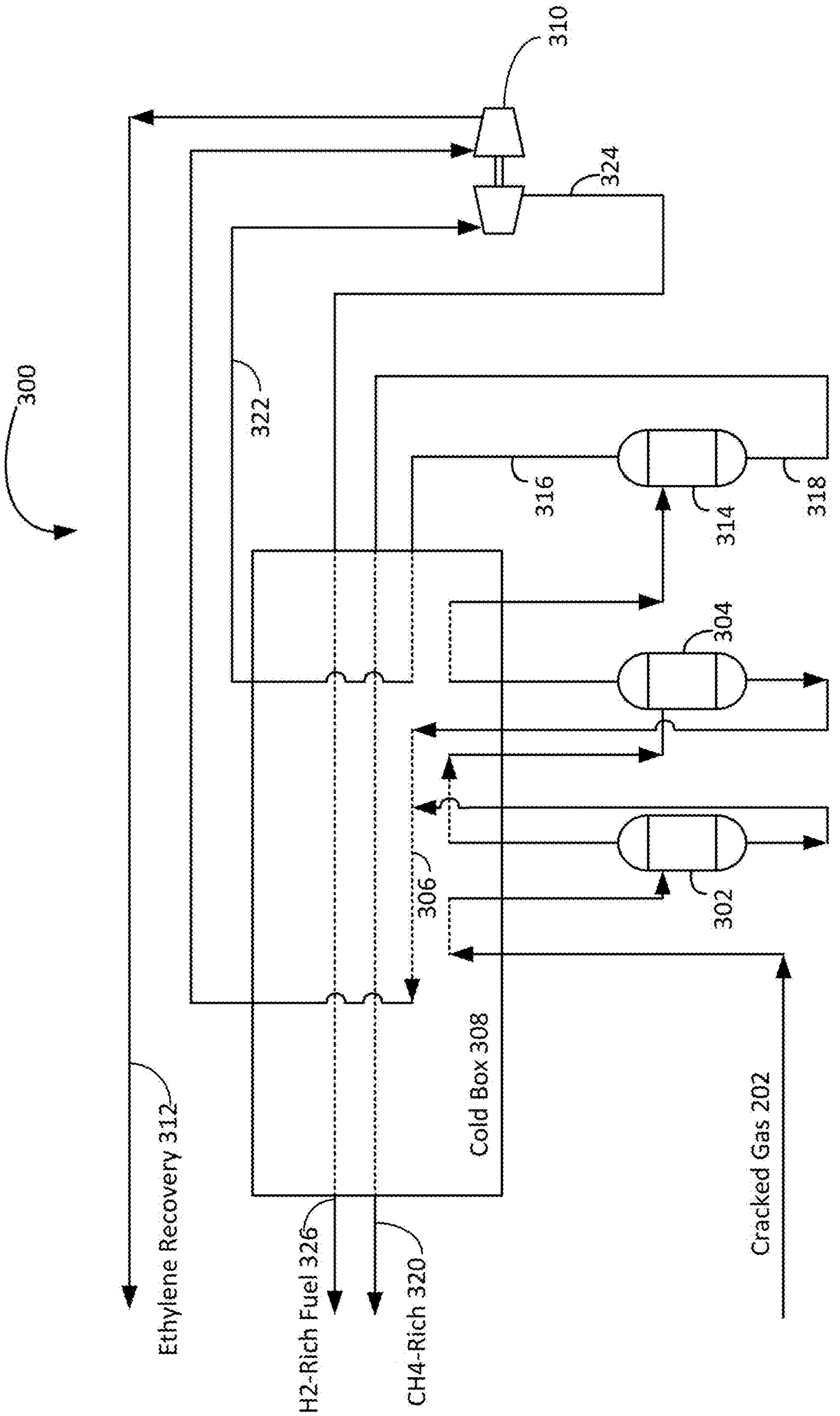
FIG. 3 shows an improved recovery section process for a steam cracking process, which yields a hydrogen-rich stream as a fuel stream fora steam cracker.

FIG. 3 illustrates an embodiment of an improved recovery section process 300 for an ethane cracking process. The cracked process gas from the steam cracker (line 202) comprises H2, CH4, and ethylene. The cracked gas enters the illustrated process, typically at a temperature of about −73° C. The cracked gas process stream 202 is cooled in the cold box 308. It should be noted here that the temperatures and pressures in this description of the process 300 are only illustrative of a particular embodiment of the process. Depending on design constraints and considerations, the temperatures/pressures may vary, as will be appreciated by a person of skill in the art. It should also be noted that the cold box 308 may include other hot and cold lines that, in the interest of clarity, are not illustrated here.

The process gas stream 202 is progressively cooled and knock-out drums 302 and 304 are used to remove ethylene from process gas. The cooling temperatures can be configured to manage the approach temperatures in the cold box. According to some embodiments, the temperature of the first knock-out drum 302 may be about −115° C.±10° C. and the temperature of the second knock-out drum may be about −130 to about −145° C. The bottom streams of the knock-out drums 302 and 304, which are enriched in ethylene, can be combined into an ethylene-rich stream 306. The ethylene-rich stream 306 can be recompressed using a turbo expander/compressor 310 to provide an ethylene-rich ethylene recovery stream 312. The top streams of the knock-out drums 302 and 304, which are enriched in CH4 and H2 (i.e., tail gas), can be further cooled in the cold box and provided to a third knock-out drum 314. According to some embodiments, the temperature of the third knock-out drum 314 may be about −163° C.±10° C. The top stream 316 from the third knock-out drum 314 is enriched in H2. The bottom stream 318 from the third knock-out drum 314 is enriched in CH4. The temperature of the third knock-out drum 314 determines how much CH4 is knocked out, i.e., it determines the purity of the H2 stream. The CH4-enriched bottom stream 318 is reheated in the cold box and exits the system as a CH4-rich stream. The H2-enriched top stream 316 is reheated in the cold box to provide a reheated H2-enriched stream 322. According to some embodiments, the temperature of the reheated H2-enriched stream 322 can be about −140° C. and its pressure can be about 20 to about 35 barg. Stream 322 is expanded using the turbo expander/compressor 310 to yield an expanded H2-enriched stream 324. This drops the temperature and pressure of the expanded H2-enriched stream 324. For example, according to some embodiments, the temperature of stream 324 may be about −177° C. and the pressure may be less than about 10 barg, for example about 6 barg. The expanded H2-enriched stream 324 is reintroduced to the cold box 308, thereby providing a cold stream within the cold box capable of providing an adequate temperature approach to effect the separation of CH4 and H2 in the knock out drum 314. The expanded H2-enriched stream 324 ultimately exits the cold box as H2-rich fuel stream 326, which can be sent back to the furnace to provide H2-rich fuel for the burners. According to some embodiments, the H2-rich fuel stream 326 may comprise greater than 90 mol % H2, or greater than 95 mol % H2, with most of the remainder comprising CH4. According to some embodiments, the recovery section process 300 may recovery over 90% or over 95% of the H2 available in the cracked gas process stream.

Whereas the typical recovery section process 104 (FIG. 2) produces a single tail gas stream 214, which comprises both H2 and CH4, the improved recovery section process 300 (FIG. 3) splits the tail gas into a hydrocarbon-rich stream (e.g., a CH4-rich stream) 320 and a H2-rich stream 326. This allows the H2-rich stream to be preferentially used as fuel for the furnace burners, thereby reducing CO2 emissions from the furnace. It should be noted that processes exist in the prior art for isolating H2 from cracked process gas. Those prior art processes are typically used to isolate H2 as a commodity gas, not to use as fuel for the burners. The prior art processes typically sacrifice a portion of the H2 by reinjecting it into the CH4-rich stream to lower the liquid stream vaporization temperature. As a result, the prior art processes can typically only recover about 80-85% of the available H2 from the tail gas. Such sacrificial use of a portion of the H2 is necessary because in the typical process there is not a stream in the cold box having a temperature cold enough to provide a thermal driving force to effect the separation of the CH4 and H2. The inventors have discovered that an adequate temperature approach can be achieved by expanding the reheated H2-enriched stream 322 from a high pressure of about 20 or more barg to a low pressure of about 10 or less barg and then providing the expanded (and thereby cooled) H2 stream back into the cold box to provide the appropriate temperature approach. It should also be noted here that the expansion/cooling process used in the process 300 would not likely be appropriate in applications where the purpose of isolating the H2 is to capture it as a product stream. In such H2 capture processes the H2-rich stream would typically be provided to a capture operation, such as a pressure swing adsorption (PSA) process. Such processes need a high pressure H2-rich stream as an input, so dropping the pressure of the stream, as is done in the process 300, would not be appropriate for H2 capture. But, since the H2-rich fuel stream 326 of the process 300 is meant to be burned in the furnace burners, the lower pressure is ideal.

Table 1 shows a comparison of simulations performed using recovery section processes similar to processes 104 and 300. In the simulation, the process 104 generates a single tail gas stream that comprises 84.6 mol % H2 (14,899 kilograms per hour) and 14.86 mol % CH4 (20,816 kilograms per hour). Burning the process 104 tail gas in furnace burners provides 689.6 giga-calories per hour of fire duty and produces 88.6 kilograms of CO2 per giga-calorie produced. The process 300 produces an H2-rich stream that comprises 14,857 kilograms per hour of H2 and 6,287 kilograms per hour of CH4. Burning the process 300 H2-rich stream in the furnace burners provides 501.1 giga-calories per hour of fire duty and produces 34.7 kilograms of CO2 per giga-calorie produced.

TABLE 1 recovery section process comparison.

| | Process 104 | | Process 300 | | |
|---|---|---|---|---|---|
| | Tail Gas | Mol % | H2-Rich | Mol % | CH4-Rich |
| H2 (kg/h) | 14,899 | 84.60 | 14,857 | 94.91 | 42 |
| CO (kg/h) | 101 | 0.04 | 86 | 0.04 | 15 |
| CH4 (kg/h) | 20,816 | 14.86 | 6,287 | 5.05 | 14,529 |
| C2H2 (kg/h) | 1,225 | 0.50 | 7 | 0.00 | 1218 |
| Flow (kg/h) | 37,042 | 100.00 | 21,238 | 100.00 | 15,804 |
| Fire Duty (Gcal/h) | 689.6 | | 501.1 | | 188.5 |
| kg CO2/Gcal | 88.6 | | 34.7 | | 231.9 |

As shown in Table 1, in the simulations, separating the tail gas into a H2-rich fuel stream and using that stream as fuel for the furnace burners resulted in a greater than 50% reduction in CO2 produced by the burners. Notice, however, that the available fire duty is also reduced when only the H2-rich stream is used as fuel. Accordingly, some embodiments of the disclosed steam cracking processes may involve optimizing the system to compensate for the loss of fired duty.

Figure 4:
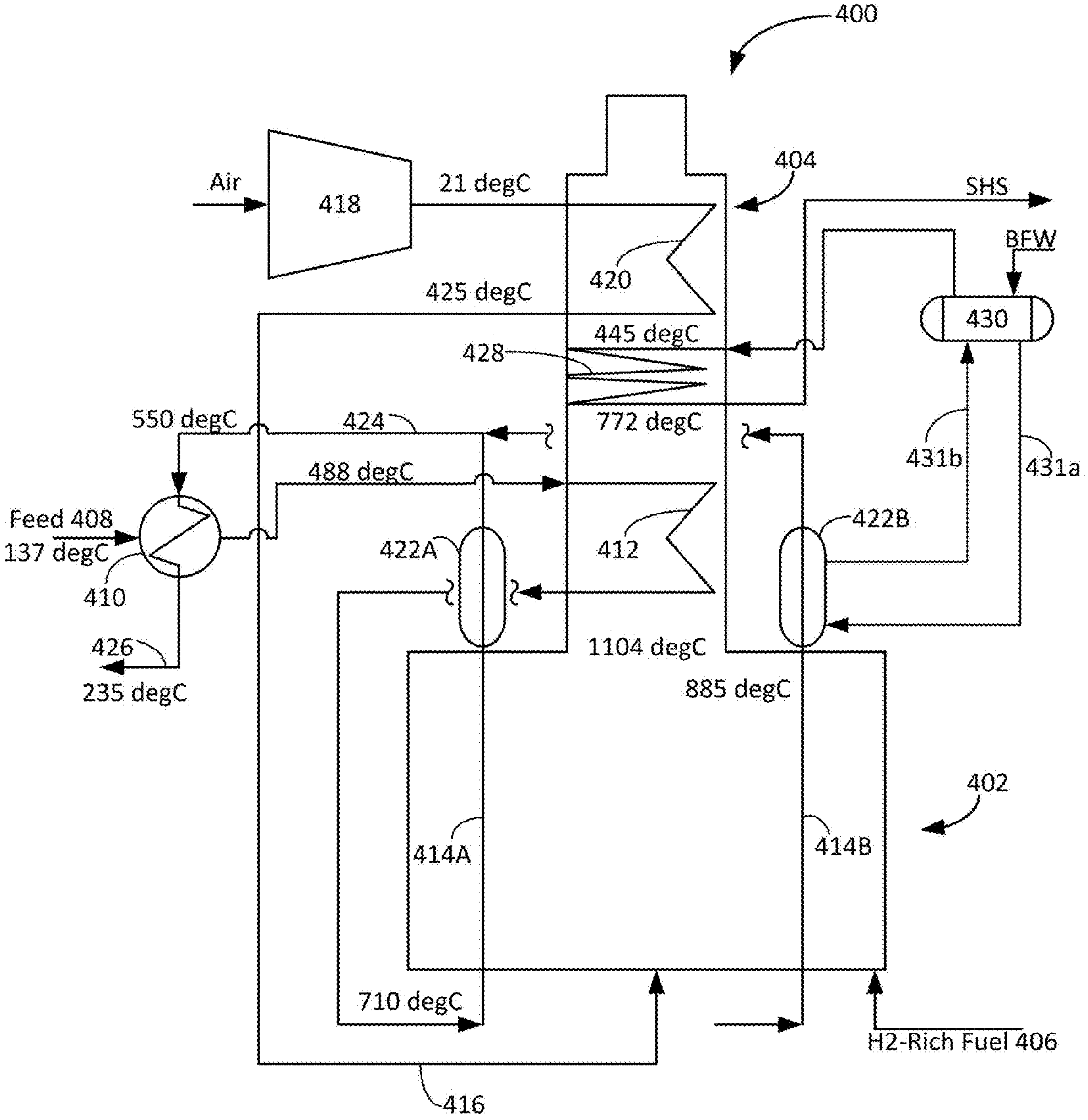
FIG. 4 shows an embodiment of a furnace configured for low CO2 emission steam cracking.

FIG. 4 illustrates an embodiment of a furnace system 400 that is configured to burn H2-rich fuel, as described above. Temperatures are shown at various locations within the systems, in degrees Celsius (deg C.). It should be appreciated that the illustrated temperatures are only illustrative and other embodiments may use other temperatures.

The furnace system 400 comprises a radiant section (a.k.a., a fire box) 402 where fuel is burnt in burners (not shown) and a convection section 404 where heat from hot flue gas can be recovered for various heating processes, as described below. Fuel is provided for the burners via line 406. As described above, the fuel may comprise a H2-rich stream isolated from a recovery section process 300 (FIG. 3). Accordingly, the burners should be configured for burning H2, as is known in the art.

Combustion air is provided to the furnace via line 416. One way of optimizing the system to compensate for the decrease in available fire duty when using only H2-rich fuel is to preheat the combustion air. In the illustrated furnace system, combustion air is provided by a blower 418 at a temperature of 21° C. According to some embodiments, the air is preheated to a temperature of at least 350° C. The air is preheated in an air preheater 420 (to a temperature of 425° C. in the illustration) using heat from the flue gas in the convection section. Heating the combustion air reduces the available heat for some of the other heating requirements, such as for heating of process feed and for steam generation that would otherwise be provided by the fire duty of the furnace burners.

Feed, comprising steam and an ethane-rich hydrocarbon enters the furnace system 400 via the feed line 408. In the illustrated embodiment, the feed is first preheated using a feed/effluent exchanger 410 and then is further heated using a feed preheater 412 within the convection section 404. According to some embodiments, the feed preheater may heat the feed to at least 650° C. In the illustrated embodiment, the feed is heated to 710° C. The preheated feed is then passed through the radiant section of furnace via tubes 414A and 414B where the cracking reaction occurs to make product. Two radiant rows are illustrated in the drawing, but it should be appreciated that more or fewer radiant rows may be used.

Once the feeds have passed through the radiant section of the furnace, the product streams are coaled in primary quench exchangers 422A and 422B. The product streams are combined in a combined product stream 424, which is used to preheat the incoming feed stream 408 in the feed/effluent exchanger 410. The product stream exits the system as product output stream 426.

In the illustrated embodiment, the flue gas is used to heat the combustion air in the air preheater 420 and the feed in the feed preheater 412. The flue gas is also used to heat steam in a steam superheater 428 to produce superheated steam (SHS). In the illustrated embodiment, saturated steam is provided to the steam superheater 428 by heating boiler feed water (BFW) from the steam drum 430. The quench exchangers 422A and 422B can be used to heat the BFW to provide the steam, which is subsequently superheated to provide the SHS. In the illustrated embodiment, BFW is provided to the quench exchangers 422A and 422B via line 431*a* and partially vaporized BFW/steam returns to the steam drum 430 via line 431*b*. The similar piping to and from the quench exchanger 422A is omitted for clarity. Recall, since the furnace burners only burn the H2-rich fuel stream instead of burning the entire tail gas stream, the furnace fire duty is reduced. That provides less flue gas heat in the convection section 404 to perform the required heating services.

Another way in which the system 400 can be optimized to accommodate the decrease in fired duty is by balancing the feed preheating duty between the feed/effluent exchanger 410 and the feed preheater 412. In a traditional system without combustion air preheat having a greater fired duty, the primary quench exchangers 422A and 422B may be used to extract a significant amount of heat out of the reacted feed to produce steam. Secondary quench exchangers may also be used to further extract heat from the feed to increase steam generation. But in the system 400, the quench exchangers may be configured to extract less heat, thereby leaving the combined product stream 424 with more heat available to heat the feed stream 408 in the feed/effluent exchanger 410. According to some embodiments, the feed/effluent exchanger 410 may be configured to heat the feed stream to at least 350° C. Notice that the feed stream 408 is heated from 137° C. to 488° C. in the illustrated embodiment. This preheating using the feed/effluent exchanger offloads some of the heating requirement from the feed preheater 412, which, in turn leaves more heat in the convection section available for superheating process steam in the superheater 428 and for combustion air preheat 420.

The inventors have found that using aggressive combustion air preheating and feed heating in the feed/effluent exchanger can reduce the heating requirement of a modeled furnace to within the available fire duty provided by the H2-rich fuel stream produced using process 300 (Table 1). In other words, the furnace fired duty requirement can be satisfied by using only H2-rich fuel isolated from the tail gas. This enables the system to operate at less than 30% of the CO2 emissions of the base (traditional) system.

As described above, according to some embodiments, the furnaces produce substantially less steam. An option to compensate for this and maintain steam balance is to convert one or more of the major compressors from steam turbine driver to electric motor drive. According to some embodiments, power may ideally come from renewable sources to maximize the overall CO2 emission impact.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A process for steam cracking a feed stream comprising a hydrocarbon feedstock and steam, the process comprising:

pre-heating the feed stream comprising the hydrocarbon feedstock and steam to at least 350° C. in a first heat exchanger to form a first heated feed stream;

further heating the first heated feed stream with heat from flue gas in a convection section of a furnace to form a second heated feed stream;

cracking the second heated feed stream in a radiant section of the furnace to produce a cracked gas stream comprising methane (CH4), ethylene, and hydrogen (H2);

generating steam in a second heat exchanger by heating water against the cracked gas stream to produce steam and a partially cooled cracked gas stream;

passing the partially cooled cracked gas stream to the first heat exchanger to form a cooled cracked gas stream;

separating the cooled cracked gas stream to produce a product stream enriched in ethylene and a tail gas stream enriched in CH4 and H2;

separating the tail gas stream into a CH4-enriched stream and a H2-enriched stream, wherein the H2-enriched stream comprises over 90% of the hydrogen present in the cracked gas stream;

pre-heating a combustion air to at least 350° C. in the convection section of the furnace;

mixing at least a portion of the H2-enriched stream with the pre-heated combustion air to form a combustion mixture; and burning the combustion mixture in furnace burners to produce the flue gas.

2. The process of claim 1, wherein the hydrocarbon feedstock comprises ethane.

3. The process of claim 1, further comprising expanding the at least a portion of the H2-enriched stream in an expander to produce an expanded H2-enriched stream, and mixing the expanded H2-enriched stream with the pre-heated combustion air to form the combustion mixture.

4. The process of claim 3, wherein the H2-enriched stream has a pressure of greater than 20 barg and the expanded H2-enriched stream has a pressure of less than 10 barg.

5. The process of claim 3, wherein expanding the H2-enriched stream drops the temperature of the H2-enriched stream, such that the expanded H2-enriched stream is colder than the H2-enriched stream.

6. The process of claim 5, wherein separating the tail gas stream into the CH4-enriched stream and the H2-enriched stream comprises cooling the tail gas stream by heat exchange against the expanded H2-enriched stream.

7. The process of claim 2, wherein only the H2-enriched stream is used as fuel for the furnace burners.

8. The process of claim 1, wherein the H2-enriched stream comprises greater than 90 mol % H2.

9. The process of claim 1, further comprising superheating the generated steam in one or more steam superheaters in the convection section of the furnace to produce a stream of superheated steam.

10. The process of claim 1, wherein heating the first heated feed stream in the convection section of the furnace comprises heating the first heated feed stream to at least 650° C.

11. The process of claim 1, wherein fuel demand of the furnace is satisfied using only the H2-enriched stream as a fuel for the furnace burners.

* * * * *